United States Patent [19]

Jones et al.

[11] 4,434,155
[45] Feb. 28, 1984

[54] BASIC ALUMINUM BROMIDE COMPOSITIONS AND METHODS USEFUL AS ASTRINGENTS OR ANTI-PERSPIRANTS

[75] Inventors: John L. Jones, North Plainfield; Andrew M. Rubino, New Providence, both of N.J.

[73] Assignee: Armour Pharmaceutical Company, Phoenix, Ariz.

[21] Appl. No.: 88,206

[22] Filed: Nov. 9, 1970

[51] Int. Cl.$^2$ ............................................. A61K 7/38
[52] U.S. Cl. ...................................... 424/47; 424/68
[58] Field of Search .................... 424/47, 68, 65, 66, 424/154, 46, 157; 23/50

[56] References Cited

U.S. PATENT DOCUMENTS

| | | | |
|---|---|---|---|
| 1,621,528 | 3/1927 | Ellis | 424/154 |
| 2,196,016 | 4/1940 | Huehn et al. | 23/123 X |
| 2,814,584 | 11/1957 | Daley | 424/68 |
| 3,359,169 | 12/1967 | Slater, Jr. et al. | 424/68 |
| 3,476,509 | 11/1969 | Jones | 23/50 R |

*Primary Examiner*—Dale R. Ore
*Attorney, Agent, or Firm*—Ernest B. Lipscomb III W. Schwarze

[57] ABSTRACT

Basic aluminum bromides having a basicity of about 5/6 have been found to be readily soluble in cosmetic solvents such as anhydrous ethanol, to have a high degree of compatibility with halogenated hydrocarbons, and to have excellent astringent characteristics. These properties make the 5/6 basic aluminum bromides particularly suitable for use in anti-perspirant compositions, especially the aerosol sprays.

9 Claims, No Drawings

BASIC ALUMINUM BROMIDE COMPOSITIONS AND METHODS USEFUL AS ASTRINGENTS OR ANTI-PERSPIRANTS

The present invention relates to basic aluminum bromide compositions and their uses. More particularly, the invention relates to anti-perspirant compositions containing 5/6 basic aluminum bromides.

For some time now aluminum compounds have been known in the art to be useful as the active ingredient in astringent or anti-perspirant compositions and other cosmetic products. In order to be an effective astringent, it is necessary that the aluminum compound retain its ionic character when incorporated into the anti-perspirant composition. This is because it is the ionic form, not the covalent form, of aluminum which is effective as an anti-perspirant. Unfortunately, aluminum compounds which exhibit good alcohol stability and fluorocarbon compatibility generally contain aluminum in its covalent form and are therefore relatively useless as anti-perspirants.

Among the many anti-perspirants described as having the property of retarding or inhibiting the flow of perspiration, the most effective have been considered to be those containing aluminum salts of strong inorganic acids such as hydrochloric, sulfuric, sulfamic, etc. However, cosmetic preparations containing these salts have the disadvantage of irritating or burning human skin and corroding the fabric of clothing worn next to the skin. In order to substantially eliminate the corrosion of skin and clothing, the product should have a pH (in water) which is at least about 3.0, while at the same time containing a sufficient amount of aluminum in ionic form to be effective as an anti-perspirant.

With the advent of the popular aerosol dispenser for anti-perspirants, there have arisen a number of additional requirements for anti-perspirant compositions. For instance, an anti-perspirant composition must be found which is not only effective to inhibit perspiration in a safe and non-corrosive manner, but which is also compatible with the halogenated hydrocarbons which are employed to propel aerosol sprays. Furthermore, such a composition should contain a minimal amount of water so as to eliminate the extreme corrosion induced by aqueous media to the metal valves and containers, and thereby eliminate the product contamination resulting from this corrosion. Finally, the active ingredient must be capable of being dissolved in non-aqueous media in concentrations of at least ten percent (10%) by weight, since this is the generally accepted minimum concentration required for an effective anti-perspirant [When present in an aerosol, the concentration can go as low as five percent (5%) since the average formulation contains forty to sixty percent propellants which are dissipated immediately upon application, thus making a five percent (5%) formulation equal to a ten percent (10%) concentration].

One of the best anti-perspirants presently available is aluminum chlorhydroxide or basic aluminum chloride (commercially available under the trademark "CHLORHYDROL" of Reheis Chemical Company, a division of Armour Pharmaceutical Company). Unfortunately, this product has suffered from the disadvantage of insolubility in nonaqueous media, such as 95% ethanol, 100% propylene glycol, and 100% glycerine, and has been known to form highly viscous, gelatinous materials when exposed to nonaqueous alcoholic solvents. Furthermore, known hydrated forms of aluminum chlorhydroxide have been generally incompatible with flurocarbon propellants used in aerosol type dispensers, resulting in gelation of the aluminum chlorhydroxide.

Accordingly, it is an object of the present invention to find an aluminum compound having a high degree of solubility in alcohols and other organic solvents.

It is a further object of the present invention to find an alcohol soluble aluminum compound which is compatible with conventional aerosol propellants.

It is another object of the present invention to find an aluminum compound which may be used to form an effective anti-perspirant composition.

Still another object of the present invention is to provide an effective anti-perspirant composition containing an aluminum compound which requires little additional treatment or modification before incorporation into the anti-perspirant composition.

Still further objects will appear hereinafter.

It has been found that the above and other objects may be achieved with basic aluminum bromide complexes which contain one or more units of the general formula:

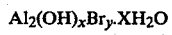

$$Al_2(OH)_xBr_y \cdot XH_2O$$

wherein x may vary from about 4.8 to 5.1 and y may vary from about 0.9 to 1.2 such that $x+y=6$, X may vary from about 2.0 to 3.4. The approximately 5/6 basic aluminum bromides of the above formula have an aluminum to bromine ratio (hereinafter referred to as the Al/Br ratio) of about 1.7 to 2.2, and preferably about 1.9 to 2.0.

It should be understood that the above formula is greatly simplified and is intended to include simple hydrated salts, polymers and other complexes or mixtures, such that the basic formula would be an average consisting of whole and/or fractional units.

Although basic aluminum bromides are old per se, it has unexpectedly been found that basic aluminum bromides are readily soluble in cosmetic solvents such as anhydrous ethanol and show a high degree of compatibility with the commonly used fluorocarbon propellants. Even more unexpected is the finding that the basic aluminum bromides are far better anti-perspirants than the presently commercially available aluminum chlorhydroxides.

The basic aluminum bromides used in the present invention may be prepared in a manner analogous to the conventional production of aluminum chlorhydroxide by reacting aluminum metal with the hydrobromic acid in water solution, or by reacting aluminum metal with a water solution of aluminum bromide. In addition, they may be prepared by reacting elemental bromine with aluminum metal in a water medium.

Whether HBr, AlBr$_3$ or Br$_2$ is used as a starting material, the first step is to prepare the equivalent of a 15 to 20% solution as bromide in a glass lined or other inert vessel equipped with agitation. With HBr, the most convenient method is adding sufficient water to 48% commercial grade HBr. In starting with AlBr$_3$, the anhydrous form is the most convenient. Initially, it is added to the vessel in the solid form and water is carefully added until the reaction subsides. Hydrated aluminum bromide could also be prepared by reacting HBr with bauxite. When liquid bromine is used as the starting material, the aluminum powder is initially slurried in the required amount of water. The bromine is carefully added after the reactor has been fitted with a reflux condenser to prevent losses due to evaporation.

Using the HBr, for example, the solution is heated to about 70° C. and aluminum powder is slowly added to the solution. Sufficient aluminum powder should be added at the start so that the exothermic reaction will produce a solution temperature of about 95° C. After the desired temperature is reached, the aluminum powder should be added in small increments such that the total addition is complete in about forty-five minutes for a 1 liter batch. For a 2 liter batch, the time would increase to about 60-90 minutes, but does not go up in proportion for still larger batches. The reaction rate and temperature can be controlled by means of heating and cooling when needed. The total amount of aluminum added for the given amount of hydrobromic acid in the solution should be slightly greater than stoichiometrically proportional to the Al/Br ratio desired in the basic aluminum bromide product.

When the powder application is complete, the temperature of the reaction mixture should be elevated to about 100° C. as rapidly as the foam level will permit. As the heat of reaction subsides, external heating will be required to complete the reaction at this temperature. When the heat of reaction starts to subside, pH readings (25° C.) should start to be taken. When the pH reaches a value of 3.0, further readings should be taken every fifteen minutes until a pH end point of 3.45 is reached. If an Al/Br ratio of about 1.9 to 2.0 is desired, the reaction should be allowed to continue for no longer than about 10 to 15 minutes beyond the pH endpoint before filtering. If higher or lower Al/Br ratios are desired, a correspondingly higher or lower pH endpoint is used.

Next, the reaction mixture is filtered through the equivalent of a No. 5 Ertel filter pad at about 20 PSI. This filtration will require about 10 to 15 minutes and the clear, water-white filtrate will have, or should be adjusted to, a specific gravity of about 1.46. A typical assay range of this product will be:
11.1-11.9% aluminum
16.9-17.8% bromide
Al/Br Ratio=1.9-2.0

Finally the aqueous solution of basic aluminum bromide must be dried to a solid. While drying is the most critical part of the preparation, the particular method of drying does not appear to be particularly critical. For example, products having high alcohol stability and good fluorocarbon compatibility have been produced using air drying at room temperature or spray drying. However, excellent results have been achieved with rapid vacuum drying, for example using a rotary vacuum dryer at a pressure of about 20 mm of mercury and a maximum external temperature of about 35° C. For this procedure, the normal drying time is about 3.5 to 4 hours.

Although the quantity of water present in the final basic aluminum bromide product does not appear to be as critical as with the basic aluminum chlorides, care must be exercised to prevent the product from becoming overdried to the point of alcohol insolubility. Basic aluminum bromide solids having a calculated water content in the range of about 14 to 22 weight percent, and preferably about 16-18 weight percent, have been found to be highly satisfactory. A typical product would be off-white and would have an assay within the following ranges:
19.0-21.0% aluminum
28.0-32.0% bromide
Al/Br ratio=1.7-2.2
19-25%: water by Karl Fischer
14-22%: water by calculation*

*The theoretical amount of free and coordinated water is calculated by solving the following equation for mols [OH]:

$$mols[OH] + mols[Br] = 3[mols\ Al]$$

and then subtracting the weight percents of OH, Br and Al from 100 percent.

Since water contents determined by Karl Fischer titrations have shown large discrepancies and somewhat inconsistent results, it is the theoretical calculated water content which is generally reported and referred to in the following examples and the rest of the application. All percentages given in this application are by weight unless otherwise specified.

The basic aluminum bromides used in the present invention may be understood more fully with reference to the following specific examples:

EXAMPLE I

Into a 4 liter glass lined container equipped with agitation was added 505 grams of reagent grade 48% hydrobromic acid and 830 grams of deionized water. The solution was heated to about 70° C. and aluminum powder was added to expedite attaining a temperature of 95° C. A total of 172 grams of aluminum powder was added in increments during the preparation such that reactivity did not become too vigorous. The temperature was raised to as high as 100° C. in order to experdite dissolution of the aluminum and the reaction was carried to a pH (25° C.) endpoint of 3.45, during which the net weight of the reactants was adjusted to about 1500 grams. The reactants were filtered within 15 minutes of the endpoint. After filtering, the filtrate was rotary vacuum dried to about 50% of its weight to yield solids assaying: 19.5% Al, 28.3% Br, 24.8% $H_2O$ by Karl Fischer (21.4% by calculation) and Al/Br ratio=2.05. The solids were soluble to the extent of 30% in anhydrous ethanol (SDA-40) in less than one half hour and had a carbon tetrachloride compatibility (defined as the number of cc.'s of carbon tetrachloride to effect a permanent cloudiness to 60 grams of a 30% solution of the product in anhydrous ethanol) of about 111 cc.

EXAMPLE II

To 830 grams of water was added 505 grams of 48% hydrobromic acid (HBr). The HBr was reacted with 172 grams of aluminum powder as in Example I. An end point pH of 3.5 was reached in 3.25 hours. The filtrate assayed 10.75% Al and 15.9% Br and had a viscosity of 12.5 cp., a specific gravity of 1.415, and a pH of 3.55. A 1,000 gram sample of the filtrate was air dried at room temperature to a constant weight of 540 grams. The resulting solids were quite soluble in anhydrous ethanol and had a $CCl_4$ compatibility of 149 cc. The solids assayed 20.42% Al, 29.5% Br, 17.8% $H_2O$ (calculated) and Al/Br ratio=2.05.

EXAMPLE III

Another sample was prepared in the same manner as in Example II but using more Al powder, and a sample of the filtrate was spray dried at 150° F. The resulting solids were quite soluble in anhydrous ethanol, had a $CCl_4$ compatability of 115 cc, and assayed 20.3% Al, 27.2% Br, Al/Br ratio=2.21 and 19.9% $H_2O$ (calculated).

EXAMPLE IV

To a reactor containing 715 grams of 99.9% Al pellets was added 430 grams of H$_2$O and 320 grams of 48% HBr. The mixture was reacted for a total of twelve hours and left to stand over two nights, reaching an end point pH of about 3.6. The solution assayed 11.5% Al, 16.1% Br and an Al/Br ratio of 2.11. A 100 gram sample was dried at room temperature to a constant weight of 57.1 grams which assayed 20.1% Al, 28.1% Br and 19.8% H$_2$O (calculated). The solids had a CCl$_4$ compatibility of 127 cc.

EXAMPLE V

Water was added dropwise to a reactor containing 97 grams of anhydrous AlBr$_3$ until conversion to the hydrate was complete; then the total water content was increased to 650 g. The aqueous bromide solution was then reacted with 47 g of aluminum powder as in Example I. In order to assure completion of the reaction, an additional 5 g of aluminum powder was added, and the mixture was filtered after 15 minutes. A portion of the clear filtrate was rotary vacuum dried at ambient temperatures and about 10 mm Hg pressure to yield an off-white solid assaying 20.5% Al, 31.2% Br, Al/Br=1.95, and which was readily soluble in anhydrous ethanol.

EXAMPLE VI

Into a one-liter glass reactor equipped with agitation and a reflux condenser were added 54 g of aluminum powder and 650 g of deionized water. To the agitated slurry maintained at ambient temperatures was added 84 g of liquid bromine over a period of 30 minutes. The temperature was increased to about 95° C. and maintained for a period of 2 hours, after which the reaction was virtually complete. In order to assure completion of the reaction, an additional 5 g of aluminum powder was added, and the reactants were filtered after 15 minutes. The clear filtrate was dried to a friable solid in a rotary vacuum dryer. The solid was readily soluble in anhydrous ethanol and assayed 20.7% Al, 30.9% Br, 15.9% H$_2$O (calculated) and Al/Br=1.98.

EXAMPLE VII

Another product was prepared as in Example II only using less aluminum powder. A sample of the filtrate was rotary vacuum dried at ambient temperature to give a solid which assayed 18.9% Al, 32.0% Br, Al/Br=1.75 and 20.2% H$_2$O (calculated). The product was readily soluble to the extent of at least 30% in anhydrous SDA-40 and had a CCl$_4$ compatibility of 207 cc.

The basic aluminum bromide compounds used in the present invention have solution characteristics which compare quite favorably and unexpectedly with aluminum compounds presently or previously used in antiperspirant compositions. For example the solids prepared in Example I were soluble to the extent of 30% in anhydrous ethanol (SDA=40) in less than 0.5 hours and had a CCl$_4$ compatibility of 111 cc. Both of these values are comparable to those for the glycol complex basic aluminum halides described in U.S. Pat. No. 3,420,932.

By contrast, a spray dried alcohol soluble basic aluminum chloride, prepared according to our copending application Ser. No. 84,093, filed Oct. 26, 1970, now U.S. Pat. No. 3,904,741, entitled "Alcohol Soluble Basic Aluminum Chlorides and Method of Making Same" assigned to the same assignee as the present invention, having an assay of 24.6% Al, 17.04% chloride, 22.5% water by Karl Fischer (20.0% by calculation), and an Al/Cl ratio of 1.90, requires about six hours to dissolve to the extent of 30% in SDA=40 and has a CCl$_4$ compatibility of 74 cc's. Another interesting comparison is that a 56% alcohol solution of basic aluminum bromide has a viscosity of about 200 centipoises (cps), whereas a 40% solution of the alcohol soluble basic aluminum chloride has a viscosity of about 300 cps. Also, from the standpoint of cosmetic acceptability, the skin drying characteristics (i.e., tackiness or stickiness) of the basic aluminum bromide are superior to either the alcohol soluble basic aluminum chloride or the glycol complexed basic aluminum halides. The basic aluminum bromides are further characterized by the following solvent solubilities:

SDA-40 (anh.)—56% (g/100 g soln.)
Propylene Glycol—47.5%
Isopropyl Alcohol—3.3%
Dioxane—1.3%
n-Butanol—0.66%
Isopropyl Myristate—0.0
DMSO—0.0
Hexadecyl Alcohol—0.0

In preparing the astringent for anti-perspirant compositions of the present invention, solutions of the basic aluminum bromides in non-toxic dermatologically acceptable nonaqueous solvents may be combined with any of the conventional aerosol propellants, including the fluorocarbon compounds which are commercially available from E. I. duPont de Nemours & Co. under the Freon trademarks. Examples of suitable propellants include trichloromono-fluoromethane (Freon 12), dichlorotetrafluoroethane (Freon 114), monochlorodifluoromethane (Freon 22), trichlorofluororethane (Freon 113), octafluorocyclobutane (Freon C 318), pentafluoromonochloroethane (Freon 115), dimethyl ether, vinyl chloride, nitrous oxide, nitrogen, 1,1,1-chlorodifluoroethane. It should be noted that in the carbon tetrachloride compatibility test used in the above examples, approximately 3 cc of CCl$_4$ is equivalent to 1 cc of a 60/40 mixture of Freon 12 and Freon 114.

In order to test the aerosol formulations of the present invention for corrosion, stability and valve clogging, a number of tests were run according to the following examples:

EXAMPLE VIII

A basic aluminum bromide solid, similar to that prepared in Example I, was made up according to the following formulation:
210 grams Basic Aluminum Bromide (BAB)
90 grams Hexadecyl Alcohol
30 grams Silicone Fluid 1066 (General Electric)
30 grams Stearic Acid
9 grams Perfume
1130 grams SDA-40

The formulation was prepared by adding the hexadecyl alcohol, silicone fluid, stearic acid and perfume to the SDA-40 and mixing (for example using a Premier Mill Dispersator with a 1 inch Duplex Head at an average speed of about 4000 rpm) until the solution was clear. The basic aluminum bromide was then added to the solution and again mixed until clear. The above 14% solution of basic aluminum bromide was then mixed with a 60/40 mixture of Freon 12 and Freon 114 to produce an approximately 7% basic aluminum bromide aerosol formulation. Aerosol cans from American Miraspra (DX20, J4 lined, BX4 LSC with OEL 500 TSS valves) were filled with 75.5 grams of the 14% solution and 55.4 mls of the propellant mixture. Similarly, bottles were filled with 25 grams of the 14% solution and 18.1 mls of the propellant mixture. After one and a half months of spray testing there was no stoppage of spraying due to either gelling of the formulation or clogging of the valves. Also, after a month of storage of the cans at 105° F. the formulation was cloudy and yellowish green, and the can and valve showed excellent resistance to corrosion with only slight discoloring of the can lining. Similar results were observed for cans stored at ambient for one month except that no discoloration was observed. In the bottles there was a slight precipitate for samples stored at 105° F. and only a trace precipitate for samples stored at ambient.

EXAMPLE IX

A 20% solution of basic aluminum bromide was prepared according to the following formulation:
300 grams BAB
90 grams Hexadecyl Alcohol
30 grams SF 1066
30 grams Stearic Acid
9 grams Perfume (Alpine #3818)
1041 grams SDA-40
The above formulation was prepared in the same manner as in Example VIII and mixed in cans and bottles with the same amounts of propellant to produce 10% basic aluminum bromide aerosol formulations. There was a slight precipitate in bottles stored at 105° F. and a trace precipitate in bottles stored at ambient. After one and one half months no failures in the spray tests were observed. For cans stored at ambient for one month the concentrate was clear yellow and the can and valve were in excellent condition. Similar results were observed for cans stored at 105° F. for one month except that the linings were discolored and one can showed bottom peeling and soft lining.

EXAMPLE X

A 20% solution of basic aluminum bromide was prepared by adding 300 grams of the bromide to 1200 grams of SDA-40 and mixing until clear. Aerosol cans were filled with the same amount of solution and propellant as in Example VIII to produce a 10% basic aluminum bromide aerosol formulation. After about one month there were no failures in the spray tests. Also, after one month of storage at 105° F. the can, valve and formulation were in excellent condition, except that the can lining was discolored.

EXAMPLE XI

A 10% basic aluminum bromide aerosol formulation was prepared as in Example X and placed in an American Miraspra WC unlined can. After one week at 105° F. the can, valve and aerosol formulation were in excellent condition. After two weeks there was slight gellation of the formulation, but this did not affect spraying. The containers were sprayed until empty.

It should be understood that the tests in the above Examples (VIII–XI) were not exhaustive, and only 1 or 2 of the dozen or more cans prepared in each example were actually opened for observation of any corrosive effects. Accordingly, since discoloration, cloudiness, slight precipitation, etc. do not appear in all samples, it is suspected that these effects may be due to impurities in individual products or formulations or other variations among individual samples.

To evaluate the anti-perspirant effectiveness of the basic aluminum bromides as compared to other anti-perspirant compositions, an anti-perspirant test was performed by an independent concern on the ten samples shown in Table I.

The tests were performed by axillary application to thirty-six women from the Miamiville, Ohio area, who were required to abstain from the use of all anti-perspirant materials for one week prior to and throughout the tests. The study was carried out in four one week periods during the weeks of Feb. 23, Mar. 16, Apr. 6, and Apr. 27, 1970. Each of the subjects used a different sample in each of the four weeks, with sample A being the control which was used for one of the four weeks by all thirty-six subjects.

Sample applications were made by a technician to one of the axillae (armpits) of each subject after the axillae had been rinsed with tepid water to remove any soap residue. Aerosol samples D and G through J were applied by spraying the axilla for two seconds from a distance of about six to eight inches. Stick sample E was applied by rubbing over the entire axillary surface. The amount of aerosol and stick samples used was determined by weighing each container before and after each application. Solution samples A, C and F were applied in 0.6 ml portions to the axilla by means of a pre-moistened cotton swab which was rubbed over the entire axillary area. Sample B (gel) was applied in a 0.6 ml portion with a tongue depresser by rubbing over the entire axillary area. The above portions of each sample were believed to be roughly equivalent as to the amount of active ingredient applied.

Sweating was induced by seating the subjects in a room maintained at about 100° F. and at a relative humidity of about 35%. Sweat collections were made by holding weighed Webril pads against the axillae.

The sample applications and sweat collections were made according to the following schedule during each week: As a control, no sample applications were made on Monday and sweat collections were made in three successive 20 minute collection periods immediately after the subjects had entered the hot room. On Tuesday the first sample applications were made followed immediately by three 20 minute collections as on Monday. A second sample application was made following the last collection on Tuesday. On Wednesday and Thursday third and fourth sample applications were made and sweat collections were taken 1 hour after each of the applications. On Thursday the fifth sample application was made after the last collection, and on Friday the last sample collections were made 22 hours after the fifth sample application.

In all cases sweating ratios were calculated by dividing the amount of sweat collected from the test axilla by that obtained from the control axilla. Mean control sweating ratios were calculated using the results from all of the control days. Adjusted ratios were then calculated by dividing the individual ratios by the mean control ratio for each subject. These adjusted ratios were converted to percent reduction in sweating rates by the following formula:

$$100 \times (1.000 - \text{adjusted ratio})$$

The percent reductions in sweating observed after one, three, four and five applications of the test materials are shown in Table II. The 95% confidence limits of these values are omitted, but range from about 4 to 15%.

Mean values determined after three and four applications and after five applications were adjusted on the basis of the relative response of the three test groups to the anti-perspirant activity of sample A. These mean values were calculated using the ratios of mean reductions observed in each group to the mean reduction for all thirty-six subjects. The resulting adjusted mean values are shown in Table III.

As can be seen from Tables II and III the basic aluminum bromide sample (F) was considerably more effective than any of the basic aluminum chloride samples (A, C and D). Furthermore, the basic aluminum bromide sample showed anti-perspirant activity which was superior to every other sample tested except for the adjusted mean value of sample H. It should be noted also that there was no significant axillary irritation observed in any subject for any sample during the test period.

TABLE I

| Sample No. | Sample |
|---|---|
| A | 20% w/w Chlorhydrol Aqueous Solution |
| B | Chlorhydrol Derivative Gel |
| C | 20% w/w Alcohol Soluble Chlorhydrol in Anhydrous Ethanol Solution |
| D | Aerosol Formulation of 3.5% Pulverized Dried Basic Aluminum Chloride, 6.2% Isopropyl Myristate, 0.3% Bentone 34 and 90% Propellant |
| E | Chlorhydrol Derivative Anti-Perspirant Sticks |
| F | 20% w/w Basic Aluminum Bromide Aqueous Solution |
| G thru J | Aerosol Anti-Perspirants of Four (4) Different Manufacturers |

TABLE II

| | | Application | | | | | Mean 3 & 4 | Mean 5 |
|---|---|---|---|---|---|---|---|---|
| | | 1 | | | 3 | 4 | | |
| Sample | Subjects | Hours* | | | | | | |
| | | 0 | ⅓ | ⅔ | 1 | 1 | 1 | 22 |
| A | 1–12 | 18.1 | 13.4 | 15.1 | 42.8 | 43.8 | 43.3 | 49.8 |
| A | 13–24 | 11.0 | 12.4 | 10.4 | 39.7 | 45.2 | 42.5 | 51.0 |
| A | 25–36 | 2.5 | 11.8 | 4.0 | 25.4 | 25.9 | 25.6 | 31.8 |
| B | 1–12 | 15.2 | 20.9 | 19.4 | 28.2 | 35.3 | 31.7 | 31.5 |
| C | 1–12 | 26.7 | 29.9 | 14.6 | 39.7 | 39.0 | 39.4 | 42.2 |
| D | 1–12 | 0.8 | (5.1) | (6.1) | 16.7 | 22.0 | 19.4 | 26.1 |
| E | 13–24 | 6.7 | 10.9 | 4.8 | 8.2 | 7.0 | 7.6 | 11.6 |
| F | 13–24 | 24.1 | 23.2 | 16.0 | 56.2 | 59.6 | 57.6 | 63.3 |
| G | 13–24 | 9.3 | 6.1 | 6.1 | 21.9 | 21.0 | 21.5 | 32.6 |
| H | 25–36 | 1.2 | 8.5 | 12.3 | 34.2 | 40.2 | 37.2 | 50.8 |
| I | 25–36 | 12.2 | 9.7 | 5.5 | 19.6 | 24.0 | 21.8 | 17.5 |
| J | 25–36 | 15.8 | 17.1 | 9.1 | 26.2 | 23.8 | 25.1 | 27.9 |

*Hours from treatment until start of sweat stimulation.
( ) Percent increase in sweat production.

TABLE III

| | | Applications 3 & 4 | | Application 5 | |
|---|---|---|---|---|---|
| Sample | Subjects | Unadjusted Mean | Adjusted Mean | Unadjusted Mean | Adjusted Mean |
| A | 1–12 | 43.3 | 36.8 | 49.8 | 43.8 |
| B | 1–12 | 31.7 | 26.9 | 31.5 | 27.7 |
| C | 1–12 | 39.4 | 33.5 | 42.2 | 37.1 |
| D | 1–12 | 19.4 | 16.5 | 26.1 | 23.0 |
| A | 13–24 | 42.5 | 37.0 | 51.0 | 43.9 |
| E | 13–24 | 7.6 | 6.6 | 11.6 | 10.0 |
| F | 13–24 | 57.6 | 50.1 | 63.3 | 54.4 |
| G | 13–24 | 21.5 | 18.7 | 32.6 | 28.0 |
| A | 25–36 | 25.6 | 36.9 | 31.8 | 43.9 |
| H | 25–36 | 37.2 | 53.6 | 50.8 | 70.1 |
| I | 25–36 | 21.8 | 31.4 | 17.5 | 24.2 |
| J | 25–36 | 25.1 | 36.1 | 27.9 | 38.5 |

The present invention may be embodied in other specific forms without departing from the spirit or essential attributes thereof and, accordingly, reference should be made to the appended claims, rather than to the foregoing specification as indicating the scope of the invention.

We claim:

1. A composition useful as an astringent or anti-perspirant comprising a non-toxic dermatologically acceptable nonaqueous solvent and at least five percent by weight of a basic aluminum bromide dissolved in the solvent, said basic aluminum bromide having units of the general formula:

$$Al_2(OH)_xBr_y \cdot XH_2O$$

wherein x may be from about 4.8 to 5.1 and y may be from about 0.9 to 1.2 such that x+y=6, and X may vary from about 2.0 to 3.4.

2. A composition according to claim 1 wherein the non-aqueous solvent is anhydrous ethanol.

3. An aerosol composition in accordance with claim 1 which includes an aerosol propellant.

4. An aerosol composition according to claim 3 wherein the propellant is a volatile halogenated hydrocarbon which comprises up to about 50% of the formulation by weight.

5. A composition in accordance with claim 1 in which the basic aluminum bromide comprises from about 10 to about 56% of the solution by weight.

6. A method of inhibiting perspiration comprising providing a basic aluminum bromide having units of the general formula:

$$Al_2(OH)_xBr_y \cdot XH_2O$$

wherein x may be from about 4.8 to 5.1 and y may be from about 0.9 to 1.2 such that x+y=6, and X may vary from about 2.0 to 3.4; dissolving the bromide in a non-toxic dermatologically acceptable non-aqueous solvent so that the bromide will comprise about 10 to 20 weight percent of the resulting solution; and applying the solution to the human axilla.

7. A method of inhibiting perspiration according to claim 6 wherein the solution is mixed with an aerosol propellant to yield a mixture containing not less than 5 weight percent of the bromide, and wherein the mixture is applied to the axilla in the form of an aerosol spray.

8. A method according to claim 6 wherein the solvent is anhydrous ethanol.

9. A method according to claim 7 wherein the aerosol propellant is a volatile halogenated hydrocarbon.

* * * * *

UNITED STATES PATENT AND TRADEMARK OFFICE
CERTIFICATE OF CORRECTION

PATENT NO. : 4,434,155

DATED : February 28, 1984

INVENTOR(S) : John L. Jones and Andrew M. Rubino

It is certified that error appears in the above-identified patent and that said Letters Patent is hereby corrected as shown below:

on the Title Page:
Reference to the Disclaimer filed should read,
-- The term of this patent subsequent to
September 15, 1995 has been disclaimed.--

Signed and Sealed this

Fifth Day of June 1984

[SEAL]

Attest:

GERALD J. MOSSINGHOFF

Attesting Officer

Commissioner of Patents and Trademarks